United States Patent [19]

Safi et al.

[11] Patent Number: 4,654,308

[45] Date of Patent: Mar. 31, 1987

[54] BIOREACTOR

[75] Inventors: Bechara F. Safi, Cartierville; Denis Rouleau, Ste-Dorothee; Raymond Mayer, Outremont, all of Canada

[73] Assignee: La Corporation de l'Ecole Polytechnique, Montreal, Canada

[21] Appl. No.: 746,402

[22] Filed: Jun. 19, 1985

[51] Int. Cl.$^4$ .............................................. C12M 1/14
[52] U.S. Cl. ...................................... 435/310; 34/199; 34/226; 312/209; 312/236
[58] Field of Search ................ 435/304, 310; 165/154, 165/918, 919; 34/199, 195, 192, 200, 226, 240; 312/209, 236

[56] References Cited

U.S. PATENT DOCUMENTS

| | | | |
|---|---|---|---|
| 48,570 | 7/1865 | Lippy | 34/199 X |
| 189,746 | 4/1877 | Kendall | 34/199 X |
| 1,535,465 | 4/1925 | Hackman | 34/199 X |
| 3,562,114 | 2/1971 | Steidl et al. | 312/236 |
| 3,592,668 | 7/1971 | Denk | 126/369 X |
| 3,743,582 | 7/1973 | Kitai et al. | 435/310 X |
| 4,277,561 | 7/1981 | Monget et al. | 435/304 X |
| 4,379,846 | 4/1983 | Shkidchenko et al. | 435/310 X |

*Primary Examiner*—Randall L. Green
*Attorney, Agent, or Firm*—Schwartz, Jeffery, Schwaab, Mack, Blumenthal & Evans

[57] ABSTRACT

A bioreactor for the biochemical treatment of liquids containing organic matter, comprises an elongated, upwardly extending tubular container having inlet means for receiving the liquid to be treated and outlet means for discharging the treated liquid. A plurality of spaced-apart first and second trays are alternatively arranged above one another inside the container, each tray being apertured to provide liquid flow communication between the inlet and outlet means and adapted to support a respective bed of microorganism cells capable of reacting with the organic matter. The apertures of the first and second trays are arranged relative to one another to cause the liquid to flow laterally across the respective cell beds of the trays as the liquid flows from one tray to another. The bioreactor of the invention is particularly useful for the anaerobic fermentation of aqueous solutions of fermentable sugars, such as bisulfite liquors originating from the pulp and paper industry, to produce ethanol, as well as for the biotreatment of effluents from the cheese industry to reduce the chemical oxygen demand and to produce methane which may be used in the cheese plant to satisfy part of its energy requirement.

18 Claims, 7 Drawing Figures

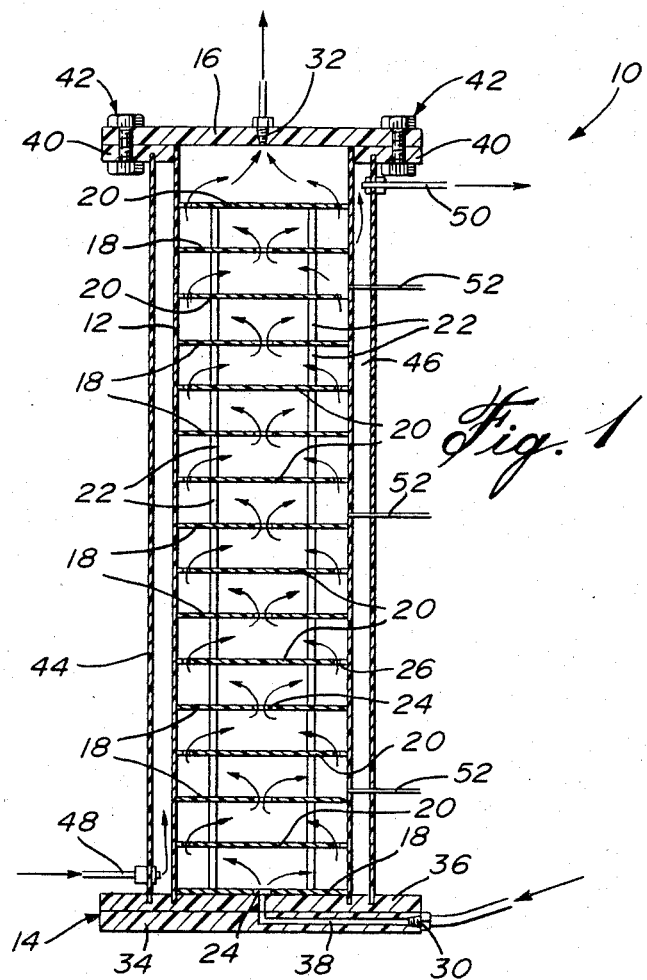
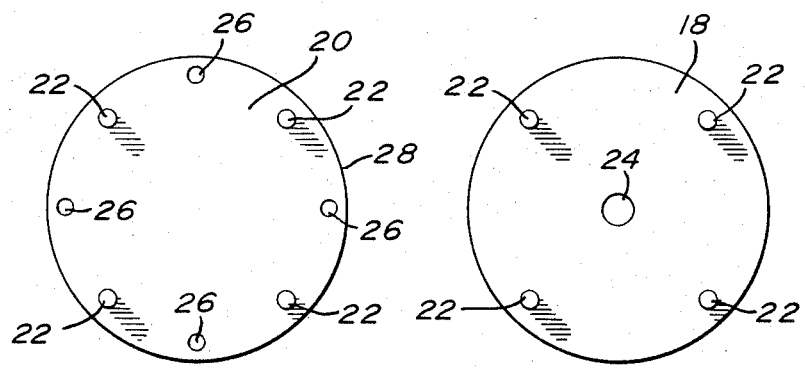

BIOREACTOR

BACKGROUND OF THE INVENTION

The present invention is concerned with a bioreactor for the biochemical treatment of liquids containing organic matter. The invention is more particularly directed to a bioreactor suitable for the fermentation of aqueous solutions of fermentable sugars, such as bisulfite liquors originating from the pulp and paper industry, to produce ethanol as a valuable by-product.

The need to treat on a profitable basis the bisulfite liquors from the pulp and paper industry is becoming more and more urgent due to the pollution regulations imposed by governments.

The annual world production of pulp by the sulfite process is about 11.5 million metric tons on dry basis, 1.5 millions of which originate from the United States and 2 millions from Canada. For each ton of dry sulfite pulp produced, there is about one ton of waste products in the form of solids dissolved in water, a major portion of this bisulfite liquor being dumped into rivers. Such a liquor has the following typical composition:

|  | % Total Solids |
| --- | --- |
| Lignosulfonate | 52 |
| Extractive matters | 3 |
| Poly and oligosaccharides | 6 |
| Monosaccharides | 23 |
| galactose: 3 | |
| glucose: 3 | |
| mannose: 11 | |
| arabinose: 1 | |
| xylose: 5 | |
| Glucuronic acid | 1 |
| Aldonic acid | 4 |
| Sulfonated sugar | 3 |
| Acetic acid | 2 |
| Methanol | 1 |
| Calcium bisulfite | 5 |
| | 100% |

The production of ethanol by fermentation of the sugars contained in the above liquor is of particular interest since the ethanol can be readily separated from the remainder of the liquid after fermentation. The conversion rate of biochemical reactions, however, is much more slow compared to the conversion rates of pyrolysis or direct combustion reactions. Thus, on an industrial scale, the use of a biochemical process necessitates a bioreactor having a high productivity.

The productivity of conventional stirred tank fermentors operated either continuously or discontinuously is limited by the specific growth rate of the microorganism cells. In a continuously operated tank-type reactor, the substrate circulates continuously through the reactor. When the medium is perfectly agitated, the cell concentration is the same everywhere in the reactor and the cells thus flow out of the reactor together with the substrate at the same concentration as in the reactor. An increase in the flow rate will therefore dilute the cells in the reactor, resulting in a lowering of the reactor productivity since the rate of product formation is proportional to the number of microorganism cells in the system. Thus, at a sufficiently high flow rate, the dilution rate will exceed the specific growth rate of the cells corresponding to the operating substrate concentration, causing the so-called phenomenon of cell washout.

On the other hand, various tubular bioreactors have been proposed, such as the free-cell reactors with or without cell recycle and the immobilized-cell reactors. In the free-cell reactor without cell recycle, the substrate and microorganism cells are introduced at the same time into the reactor, that is, at the beginning. Once the reactor is filled, the substrate circulates through the reactor. The productivity of this type of reactor is also affected by the same phenomenon of cell washout as in the continuously operated stirred tank-type reactor. When such a free-cell reactor is operated with cell recycle, it requires the additional use of a centrifugal machine in order to accomplish the cell recycle. This is not only expensive both in terms of capital investment and subsequent operating costs, but could also cause destruction of the cells. Moreover, it has been observed that the specific rate of product formation drops considerably as soon as the substrate concentration falls below 10 g/l.

By immobilizing the cells inside the reactor, using for instance a packing of gelatin coated ceramic particles treated with glutaraldehyde, the reactor can operate at a dilution rate exceeding the specific growth rate of the microorganism cells. Although such an immobilized-cell reactor has a productivity which is considerably higher than that of a free-cell reactor without cell recycle, it suffers from several disadvantages. Firstly, the film of gelatin which coats the ceramic particles swells during operation, causing a reduction of the nominal void percentage of the packing to about 50-55%. In other words, the usable volume of the reactor is only about 50% of the total real volume. The immobilization step is also very delicate and time consuming and requires additional equipment. The glutaraldehyde which serves to bind the cells to the gelatin molecules further acts as a bactericide; thus, too much glutaraldehyde could kill the immobilized cells whereas too little would allow the gelatin to dissolve in the flowing liquid to be fermented and thus cause a rupture of the bonds by means of which the cells are attached to the ceramic particles. The time required to start the reactor, after having filled the latter with the packing, disinfected the whole and inserted the cell culture, is about 8 hours; however, one must also consider the time required to recycle the packing between two cycles of operation, which is about 48 hours, Moreover, in the case of contamination, the packing including the gelatin film must be completely regenerated. Finally, there is a progressive dissolution of the gelatin film, which reduces the quantity of immobilized cells, thus resulting in a continuous lowering of the reactor productivity as a function of the operating time.

SUMMARY OF THE INVENTION

It is therefore an object of the present invention to overcome the above drawbacks and to provide a bioreactor having improved stability and productivity.

It is another object of the invention to provide a bioreactor for the biochemical treatment of liquids containing organic matter, which enables the microorganism cells to be retained inside the reactor without being immobilized while still preventing the cells from being substantially entrained by the liquid undergoing treatment.

In accordance with the invention, there is provided a bioreactor for the biochemical treatment of liquids containing organic matter, comprising an elongated, upwardly extending tubular container having inlet means for receiving the liquid to be treated and outlet means for discharging the treated liquid. A plurality of spaced-apart first and second trays are alternatively arranged above one another inside the container, each tray being apertured to provide liquid flow communication between the inlet and outlet means and adapted to support a respective bed of microorganism cells capable of reacting with the organic matter. The apertures of the first and second trays are arranged relative to one another to cause the liquid to flow laterally across the respective cell beds of the trays as the liquid flows from one tray to another.

According to a preferred embodiment of the invention, the apertures of the first and second trays are arranged to provide a radial liquid flow across the respective cell beds of the trays. For example, the first tray can be formed with a single central aperture and the second tray with at least two apertures arranged opposite one another on either side of a central longitudinal axis extending through the central aperture, whereby the liquid flows radially outwardly across the respective cell bed of the first tray and then radially inwardly across the respective cell bed of the second tray. Preferably, the second tray comprises two pairs of such opposite apertures arranged in equi-distantly spaced relation to each other adjacent a peripheral edge of the second tray.

According to another preferred embodiment, the trays are removably mounted inside the container and removable spacer means are arranged between the trays to maintain the trays in spaced relation to each other. In order to allow the trays to be readily removed from the container, the latter is advantageously provided with a removable cover which is releasably secured to the container at an upper extremity thereof. A laterally outwardly extending flange may be provided at the upper extremity of the container so as to enable the cover to be releasably secured to the flange by releasable fastener means.

In a further preferred embodiment of the invention, an outer wall spacedly surrounds the container to define therebetween an annular chamber adapted to contain a thermostatic fluid for maintaining the liquid at a substantially constant temperature.

When the bioreactor of the invention is to be used for carrying out a fermentation process, it is first properly disinfected and then simply filled with a suspension of the desired microorganism cells in sterile water at a predetermined concentration, for example 30 g/l, by first flowing such a suspension through the container and then stopping the flow to cause the cells to deposit onto the trays by sedimentation. The liquid to be treated can thereafter be fed to the reactor at a flow rate of about 5 ml/min., for example. Thus, the starting time is limited to the time required for filling the reactor. In the case of contamination, the cells can be removed from the reactor by bubbling with an air stream which creates a turbulence sufficiently high to fluidize the cells and cause the latter to flow out of the reactor without having to remove the trays. Alternatively, the trays can be removed through the top of the reactor after having removed its cover, for thorough cleaning and disinfection.

The bioreactor according to the invention eliminates the immobilization step required in the case of an immobilized-cell reactor, as well as all the equipments associated therewith. Such an immobilization step is replaced by a simple filling of the reactor with a suspension of the cells in sterile water. Moreover, the bioreactor of the invention does not necessitate any material which could have a bactericidal effect and thus kill the cells.

In the bioreactor according to the invention, the void percentage is defined by the thickness of the trays. Since the liquid undergoing treatment does not exert any mechanical strain on these trays, the thickness of the trays can be reduced and the void percentage can thus reach about 90%. Therefore, the usable volume of the reactor tends toward the total real volume.

An agitation has been observed in the liquid undergoing treatment in a bioreactor according to the invention. This agitation occurs in regions whose boundaries are defined by the upper surfaces of the cell beds and the lower surfaces of the trays, and it is caused by the gas which is formed at the surfaces of the sedimented cells as a result of the biochemical reaction (e.g. fermentation or biodegradation). When a gas bubble is liberated from the surface of a cell, a portion of the sedimented cells is projected vertically in the liquid. The cells bounce off the surface of a tray immediately located above and a majority of these cells then deposit back onto the same tray. Thus, the multi-tray bioreactor of the invention can be considered as defining a series of continuously stirred tank reactors arranged in cascade, where each tray acts not only as a mini-reactor containing a layer of active cells but also as a cell separator preventing the cells from being entrained by the liquid flow.

As mentioned previously, the bioreactor of the invention is particularly useful for the anaerobic fermentation of aqueous solutions of fermentable sugars, such as mannose, glucose and galactose, which are contained in bisulfite liquors originating from the pulp and paper industry, or other industries. It can also be used for the biodegradation of effluents containing biodegradable organic matter and may thus be useful in the biotreatment of effluents from the cheese industry for example, to reduce the chemical oxygen demand and to produce methane which can be used in the cheese plant to satisfy part of its energy requirement.

BRIEF DESCRIPTION OF THE DRAWINGS

Further features and advantages of the invention will become more readily apparent from the following description of preferred embodiments, with reference to the accompanying drawings, in which:

FIG. 1 is a longitudinal sectional view of a bioreactor according to the invention;

FIG. 2A and 2B are plan views of the two types of trays utilized in the bioreactor of FIG. 1;

DESCRIPTION OF PREFERRED EMBODIMENTS

Figure 3:
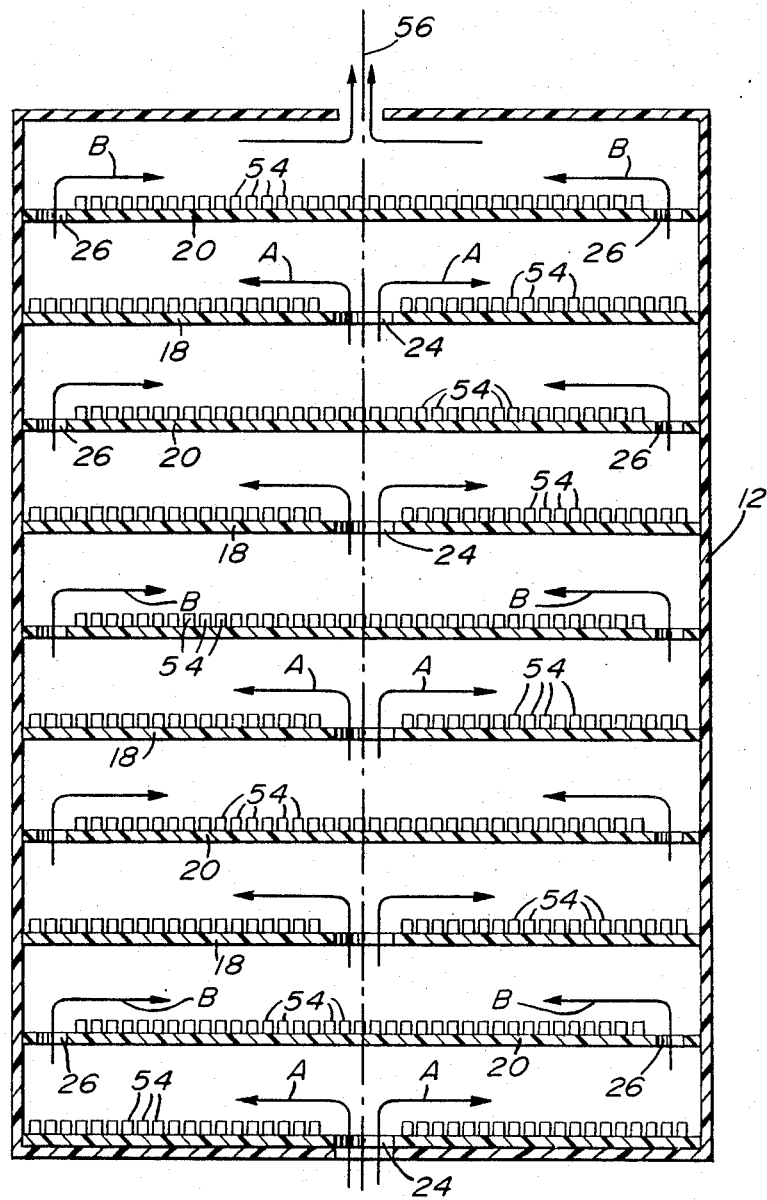
FIG. 3 is a schematic flow diagram illustrating how the liquid flows through the bioreactor of FIG. 1.

Referring first to FIG. 1, there is shown a tubular multi-tray bioreactor generally designated by reference numeral 10 and comprising an elongated, vertically-extending tubular container 12 of circular cross-section having a base 14 and a removable cover 16. Two types of planar trays 18 and 20 are alternatively arranged above one another inside the container 12. The trays 18, 20 are removably mounted inside the container in spaced relation to each other by means of removable spacers 22 consisting of ceramic cylinders arranged between the trays; the spacers 22 can be fixed to either the trays 18 or trays 20 and thus be removable therewith. As best shown in FIG. 2, the trays 18 and 20 are circular with the tray 18 being formed with a single central aperture 24 and the tray 20 with two pairs of diametrically opposite apertures 26 arranged in equidistantly spaced relation to each other adjacent the peripheral edge 28, the apertures 24 and 26 being circular. In order to provide a constant liquid flow through the reactor, the apertures 26 define a total area which is substantially equal to the area of the aperture 24.

The bioreactor 10 further includes an inlet 30 at the base 14 for receiving the liquid to be treated and an outlet 32 arranged in the cover 16 for discharging the treated liquid. As shown, the base 14 comprises two plates 34 and 36, the plate 36 serving to mount the container 12. The inlet 30 includes a conduit 38 extending through the base plates 34, 36 and opening into the central aperture 24 of the lowermost tray 18 which rests on the plate 36. The cover 16, on the other hand, is releasably secured to a laterally outwardly extending flange 40 by means of a bolt and nut arrangement 42. The outlet 32 is located centrally of the cover 16 above the uppermost tray 20.

An outer concentric wall 44 spacedly surrounds the container 12 so as to define therebetween an annular chamber 46 adapted to contain a thermostatic fluid for maintaining the liquid inside the container at a substantially constant temperature. The chamber 46 is provided with a lower inlet 48 and an upper outlet 50 for respectively receiving and discharging the thermostatic fluid, thereby allowing the fluid to circulate continuously through the chamber 46.

In the experimental bioreactor 10 shown in FIG. 1, a plurality of sampling tubes 52 are arranged at predetermined locations along the length of the reactor, each tube 52 extending through the outer wall 44 and opening into the container 12. With these tubes 52, samples can be taken and analyzed to determine the conversion rate of the substrate being treated. An industrial model, however, would not have any such sampling tubes.

Turning to FIG. 3 which schematically illustrates the liquid flow through the container 12 from one tray to another, where each tray 18, 20 is seen supporting a respective bed of microorganism cells 54, the apertures 24 and 26 of the trays 18 and 20 are arranged relative to one another to cause the liquid to flow laterally across the respective cell beds 54 of the trays as the liquid flows from a lower tray to an upper tray. Moreover, owing to the provision of a single central aperture 24 in each tray 18 and of diametrically opposite apertures 26 in each tray 20, which are arranged on either side of the central vertical axis 56 extending through the central aperture 24, the liquid flows radially outwardly across the respective cell bed 54 of each tray 18 as shown by the arrows A, and then radially inwardly across the respective cell bed 54 of each tray 20 as shown by the arrows B. Such an arrangement prevents the cells 54 from being entrained by the liquid flow and thus enables the cells to be retained inside the container 12.

Figure 4:
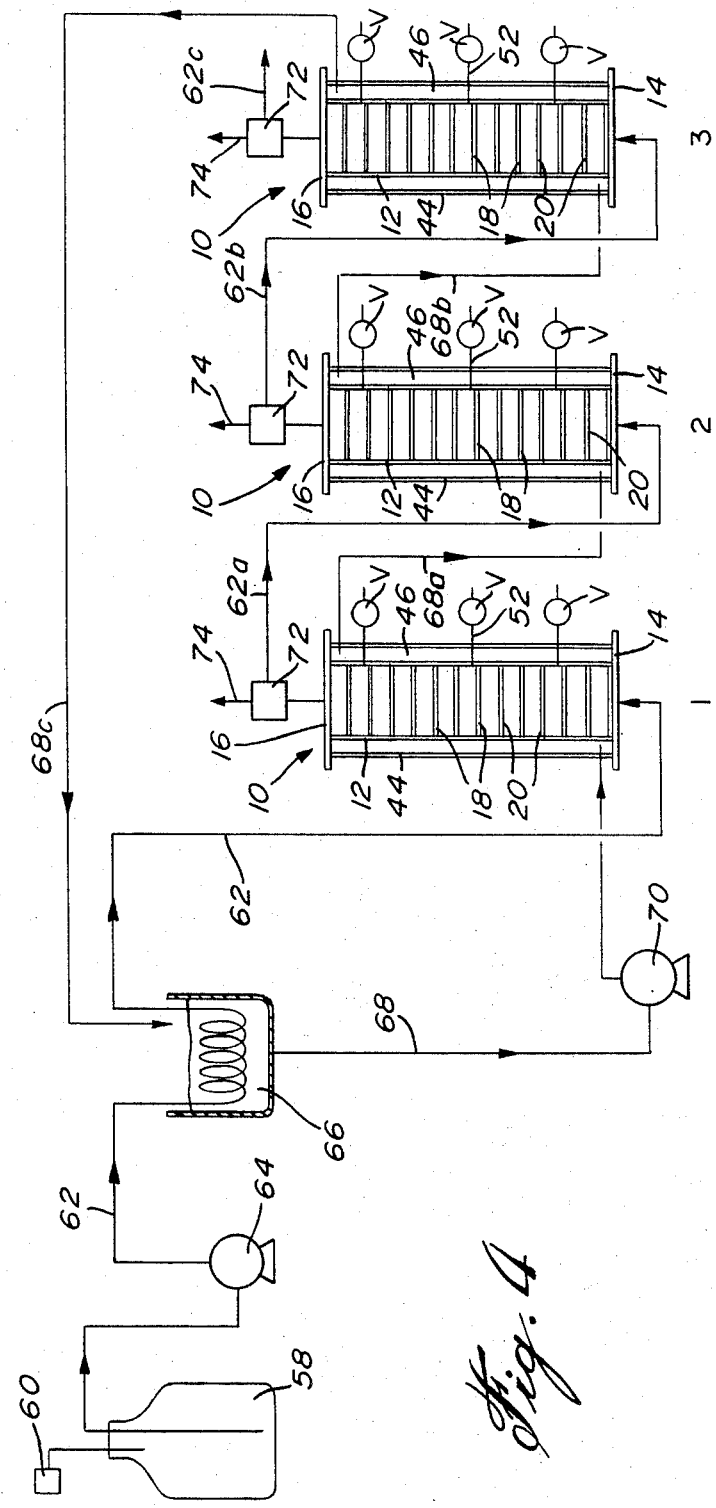
FIG. 4 is a schematic diagram illustrating how the bioreactor of FIG. 1 can be utilized for the biochemical treatment of liquids containing organic matter.

FIG. 4 schematically shows the set-up of three identical bioreactors 10 connected together for the biochemical treatment of a liquid containing organic matter. The liquid to be treated which is contained in the feed tank 58 provided with a sterile filter 60 to prevent contamination of the liquid by the ambient air is fed to the inlet of the reactor No. 1 via line 62 by means of pump 64, after having first passed through a thermostatic bath 66 containing water maintained at a constant temperature, for example 25° C. The water of the bath 66 is also fed via line 68 by means of pump 70 to the inlet of the annular chamber 46 of reactor No. 1, the outlet of which is connected via line 68a to the inlet of the annular chamber 46 of reactor No. 2, which in turn has its outlet connected via line 68b to the inlet of the annular chamber 46 of reactor No. 3, such that the water of the bath 66 is circulated through the chambers 46 of all three reactors and is then returned to the bath via line 68c. The liquid to be treated flows through the container 12 of reactor No. 1 from a lower to an upper tray and radially across the respective cell beds of the trays 18, 20, where it reacts with the cells. The mixture of gas and liquid which is produced as a result of this reaction is discharged through the outlet of the reactor and sent to a gas/liquid separator 72 which separates the gas from the liquid. The gas is vented off via line 74 and the separated liquid is fed via line 62a to the inlet of the next reactor No. 2, for further treatment. This operation is repeated twice by means of reactors Nos. 2 and 3 which are connected together via line 62b, in order to ensure a substantially complete conversion of the organic matter contained in the liquid which is finally discharged via line 62c.

It should be noted that the gas which is liberated at the surfaces of the cells as a result of the reaction creates a turbulence inside the container 12 of the reactor 10, between the trays 18 and 20, and this turbulence may cause some of the cells to be entrained by the liquid flow. However, since the reaction has greatly diminished in the reactor No. 3 and has completely stopped in the last upper trays thereof, any entrained cells will collect in reactor No. 3 which will thus act as a cell collector. Therefore, before starting a new cycle, the reactors can be repositioned so as to restore the cell balance, that is, reactor No. 3 becomes No. 1, reactor No. 1 becomes No. 2 and reactor No. 2 becomes No. 3. In the following cycle, reactor No. 2 then becomes No. 1, reactor No. 3 becomes No. 2 and reactor No. 1 becomes No. 3.

The following non-limiting examples further illustrate the invention.

EXAMPLE 1

Figure 5:
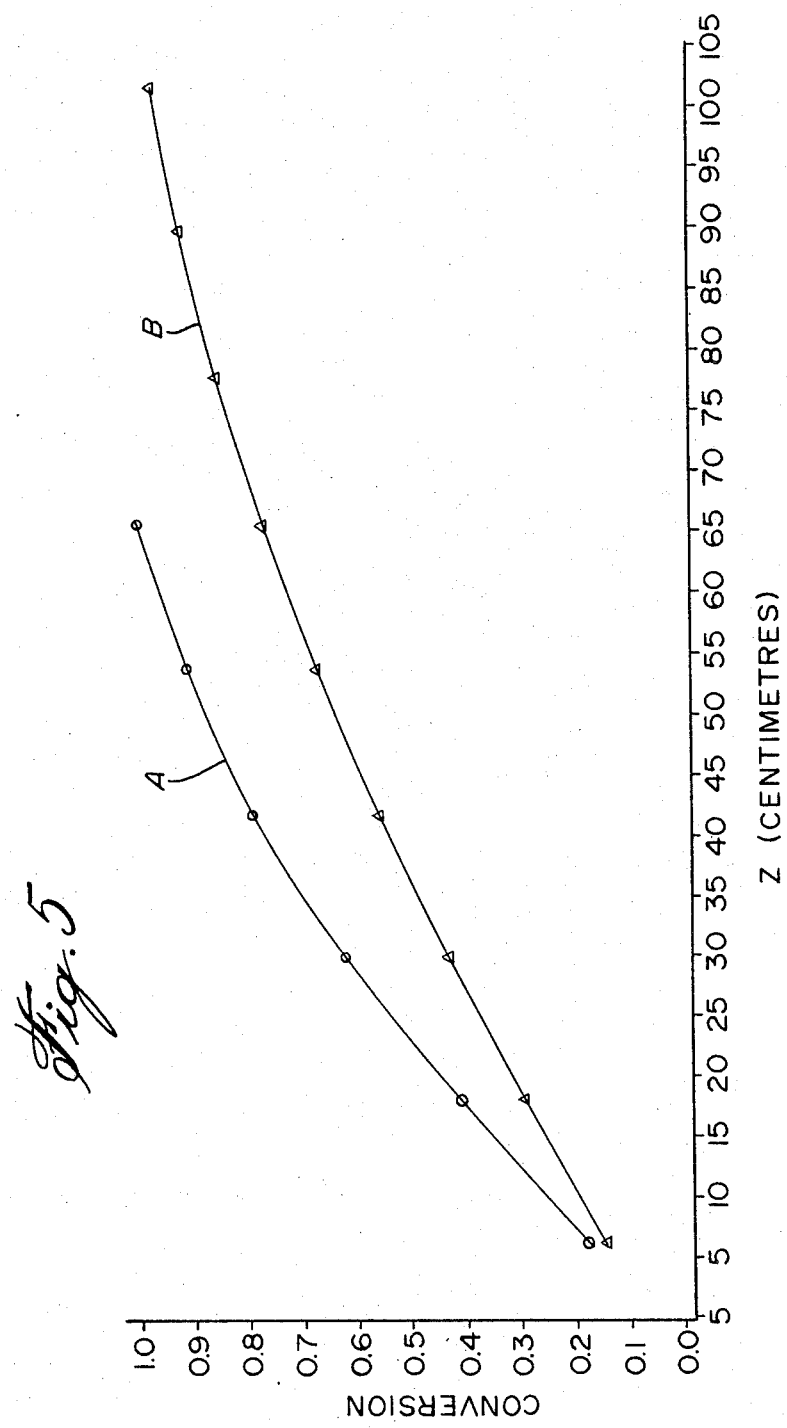
FIG. 5 is a graph showing the conversion rate of an aqueous solution of fermentable sugars as a function of the bioreactor length.

An aqueous solution of fermentable sugars was fermented at 25° C. using the system shown in FIG. 4. The solution contained 5.3 g/l galactose, 5.3 g/l glucose and 19.4 g/l mannose. Each reactor 10 had a height of 36 cm, an internal diameter of 6.4 cm and a volume of about 1 liter. The reactors were inoculated with 80 g/l of the yeast *Saccharomyces cerevisiae* and were fed with the solution at a flow rate of 5 ml/min. As shown in FIG. 5, the conversion of the sugars was substantially complete after a residence time of 5 hours (curve A) with reactors each containing 34 trays, and a residence time of 8 hours (curve B) with reactors each containing 17 trays.

This experiment was repeated with a bisulfite liquor from the pulp and paper industry and essentially the same results were obtained.

EXAMPLE 2

The system illustrated in FIG. 4 was also used for the biotreatment of an effluent from a cheese plant to reduce the chemical oxygen demand (C.O.D.) and to produce methane.

An anaerobic biomass from industrial source was used to effect the biodegradation. The reactors were inoculated with 45 g/l of volatile solids in suspension. The total volume of the reactors was about 3 liters. The effluent tested had the following composition, additives having been added to increase the alkalinity and to supplement the nitrogen and phosphorus sources:

lactoserum: 1.5 g/l
$NH_4HCO_3$: 0.0949 g/l
$NaHCO_3$: 1.7778 g/l
$KHCO_3$: 1.7778 g/l
$(NH_4)_2SO_4$: 0.556 g/l
$KH_2PO_4$: 0.0205 g/l
Yeast extract: 0.0111 g/l
pH: 8.49
alkalinity: 3900 mg/l $CaCO_3$ The reaction was carried out at 30° C. with a flow rate of 4.34 l/day, corresponding to a residence time of 16.7 hours.

The pH change as a function of the residence time was the following:

| Residence Time (h) | pH |
|---|---|
| 0 | 8.49 |
| 0.9 | 7.17 |
| 4.6 | 7.23 |
| 6.5 | 7.14 |
| 10.2 | 7.28 |
| 12.0 | 7.31 |
| 15.8 | 7.41 |

The average quantity of gases produced ($CH_4$ and $CO_2$) per day was about 2.35 liters (STP), the average proportion of methane being 73%. The production of methane per kg of C.O.D. removed was 0.3 $m^3$.

Figure 6:
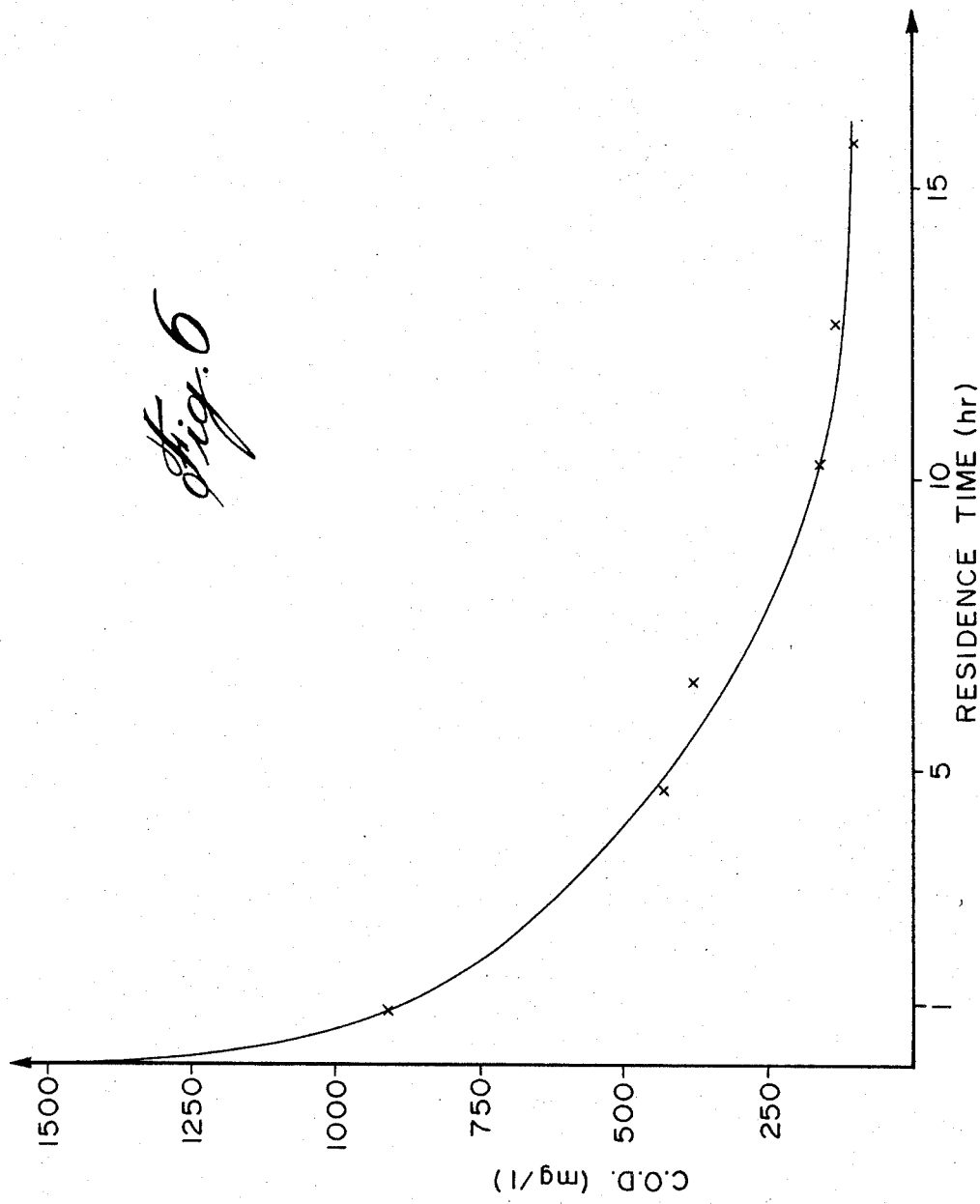
FIG. 6 is another graph showing the removal rate of the chemical oxygen demand (C.O.D.) from a cheese plant effluent as a function of the residence time in the bioreactor.

The removal of the C.O.D. as a function of the residence time which is reported in FIG. 6 was the following:

| Residence Time (h) | C.O.D. (mg/l) |
|---|---|
| 0 | 1492 |
| 0.9 | 906 |
| 4.6 | 431 |
| 6.5 | 376 |
| 10.2 | 158 |
| 12.6 | 130 |
| 15.8 | 98 |

As it is apparent from FIG. 6, the invention enables to reduce the C.O.D. by 93% and 71% of this reduction occurs in the first 4.6 hours of treatment.

We claim:

1. A bioreactor for the biochemical treatment of liquids containing organic matter, comprising an elongated, upwardly extending tubular container having inlet means for receiving the liquid to be treated and outlet means for discharging the treated liquid, a plurality of spaced-apart first and second trays, each of said first trays being arranged alternatively with said second trays inside said container, each said tray being apertured to provide liquid flow communication between said inlet and outlet means and adapted to support a respective bed of microorganism cells capable of reacting with said organic matter, the apertures of said first and second trays being arranged relative to one another to cause said liquid to flow laterally across the respective cells beds of said trays as said liquid flows from one tray to another, said trays being sufficiently close to one another such that upon reaction of said microorganism cells with said organic matter, microorganism cells projected from a bed supported by a respective one of said trays are deflected by a said tray located immediately above said respective one tray to deposit back onto said bed of said respective one tray, thereby substantially preventing said cells from being entrained by said liquid flow.

2. A bioreactor as claimed in claim 1, wherein the apertures of said first and second trays are arranged to provide a radial liquid flow across said respective cell beds.

3. A bioreactor as claimed in claim 2, wherein in each said first tray is formed with a single central aperture and each said second tray is formed with at least two apertures arranged opposite one another on either side of a central longitudinal axis extending through said central of each said first tray aperture, whereby said liquid flows radially outwardly across the respective cell bed of each said first tray and then radially inwardly across the respective cell bed of each said second tray.

4. A bioreactor as claimed in claim 3, wherein each said second tray includes two pairs of said opposite apertures arranged in, each said pair equidistantly spaced relation to the other and positioned adjacent a peripheral edge of said second tray.

5. A bioreactor as claimed in claim 4, wherein said central and opposite apertures are circular and wherein said opposite apertures on each said second tray define a total area substantially equal to the area of said central aperture on each said first tray.

6. A bioreactor as claimed in claim 1, wherein said container is circular in cross-section and each said tray has a planar circular configuration.

7. A bioreactor as claimed in claim 1, wherein said trays are removably mounted inside said container.

8. A bioreactor as claimed in claim 7, further including spacer means arranged between said trays to maintain said trays in spaced relation to each other.

9. A bioreactor as claimed in claim 8, further including a removable cover releasably secured to said container at an upper extremity thereof.

10. A bioreactor as claimed in claim 9, wherein said container is provided at said upper extremity with a laterally outwardly extending flange and said cover is releasably secured to said flange by releasable fastener means.

11. A bioreactor as claimed in claim 9, wherein said container is provided with an uppermost tray which is apertured to cause said liquid to flow radially inwardly across the respective cell bed of said uppermost tray, and wherein said outlet means is arranged in said cover centrally thereof.

12. A bioreactor as claimed in claim 1, wherein said container has a base and is provided with a lowermost tray resting on said base and having a single central aperture, and wherein said inlet means comprises a conduit extending through said base and opening into said central aperture.

13. A bioreactor as claimed in claim 1, further including an outer wall spacedly surrounding said container to define therebetween an annular chamber adapted to contain a thermostatic fluid for maintaining said liquid at a substantially constant temperature.

14. A bioreactor as claimed in claim 13, wherein said outer wall is arranged concentrically around said container.

15. A bioreactor as claimed in claim 13, wherein said annular chamber is provided with lower inlet means and upper outlet means for respectively receiving and discharging said thermostatic fluid, whereby to allow said fluid to circulate continuously through said chamber.

16. A bioreactor for the biochemical treatment of liquids containing organic matter, comprising:
   an elongated, upwardly extending tubular container having inlet means at a bottom portion thereof for receiving a flow of liquid to be treated and outlet means at a top portion thereof for discharging the treated liquid;
   a plurality of trays arranged within said tubular container, each of said trays separated from each other by a gap and having a flat surface substantially perpendicular to a longitudinal axis of said container;
   a separate bed of microorganism cells formed by gravity sedimentation and positioned on each of said flat surfaces of said trays, said beds being retained on said flat surfaces by gravity, whereby said microorganism cells are capable of reacting with said organic matter;
   and means for conveying said flow of liquid from said bottom portion of said tubular container and radially across each of said microorganism beds in series fashion, said liquid thereby being treated.

17. A bioreactor as claimed in claim 16, wherein said bioreactor includes means for preventing entrainment of said microorganism cells in said flow of liquid, said entrainment preventing means including said gap having a width sufficiently small such that microorganism cells separated from a respective said bed are returned to said respective bed through deflection against an adjacent said tray.

18. A bioreactor for the biochemical treatment of liquids containing organic matter, comprising an elongated, upwardly extending tubular container having inlet means for receiving the liquid to be treated and outlet means for discharging the treated liquid, a plurality of spaced-apart first and second trays, each of said first trays being arranged alternatively with said second trays inside said container, each said tray being apertured to provide liquid flow communication between said inlet and outlet means and adapted to support a respective bed of microorganism cells capable of reacting with said organic matter, the apertures of said first and second trays being arranged relative to one another to cause said liquid to flow laterally across the respective cell beds of said trays as said liquid flows from one tray to another;
   wherein the apertures of said first and second trays are arranged to provide a radial liquid flow across said respective cell beds;
   wherein each said first tray is formed with a single central aperture and each said second tray is formed with at least two apertures arranged opposite one another on either side of a central longitudinal axis extending through said central aperture of each said first tray, whereby said liquid flows radially outwardly across the respective cell bed of each said first tray and then radially inwardly across the respective cell bed of each said second tray; and
   wherein each said second tray includes two pairs of said opposite apertures, each said pair arranged in equidistantly spaced relation to the other and positioned adjacent to a peripheral edge of said second tray, said central and opposite apertures being circular and said opposite apertures on each said second tray defining a total area substantially equal to the area of said central aperture on each said first tray.

* * * * *